(12) United States Patent
Sergiadis

(10) Patent No.: US 11,711,882 B2
(45) Date of Patent: Jul. 25, 2023

(54) BODY CURRENT COMPENSATION SYSTEM (BODY CCS)

(71) Applicant: Georgios Sergiadis, Salonika (GR)

(72) Inventor: Georgios Sergiadis, Salonika (GR)

( * ) Notice: Subject to any disclaimer, the term of this patent is extended or adjusted under 35 U.S.C. 154(b) by 178 days.

(21) Appl. No.: 17/180,801

(22) Filed: Feb. 21, 2021

(65) Prior Publication Data

US 2022/0272824 A1    Aug. 25, 2022

(51) Int. Cl.
*H05F 1/00* (2006.01)
*G05B 15/02* (2006.01)

(52) U.S. Cl.
CPC .............. *H05F 1/00* (2013.01); *G05B 15/02* (2013.01)

(58) Field of Classification Search
CPC .............. G05B 15/02; A61N 2/02; H05F 1/00
USPC ........................................... 361/225
See application file for complete search history.

(56) References Cited

U.S. PATENT DOCUMENTS

2022/0196708 A1* 6/2022 Smith ................. G01R 19/145

FOREIGN PATENT DOCUMENTS

CN        108872898 A  * 11/2018  ............. A61B 5/055

OTHER PUBLICATIONS

Machine translation of Liu Chinese Patent Document CN 108872898 A Nov. 23, 2018 (Year: 2018).*

* cited by examiner

*Primary Examiner* — Kevin J Comber
(74) *Attorney, Agent, or Firm* — McCarter & English, LLP

(57) ABSTRACT

Problem
All conductive bodies and particularly humans bodies, living in an electrified environment are traversed by alternating currents. Especially with the rise of electromobility, these currents are also present outside the typical house or office or factory environment, influencing the body almost during the whole 24 hours life cycle.
Solution
The invention proposes simple, contactless means to protect the body, by compensating the induced currents from the electrified environment. An isolated, intermediate conductive plate between the ground and the body is used to sense and minimize the induced currents. A coil at the periphery of the intermediate plate is used to sense and compensate the induced magnetic field, in its simplest embodiment.

27 Claims, 4 Drawing Sheets

BODY CURRENT COMPENSATION SYSTEM (BODY CCS)

TECHNICAL FIELD

A61N1/3718

Aspects herein relate generally to the protection of any conductive body and particularly of the human body from external electric and magnetic fields.

BACKGROUND ART

Although humans with the same biological and anatomical features as the contemporary ones have been present on earth since many thousand years, it is practically only since the last century that humans are massively exposed to alternating electric and magnetic fields.

This exposure is the result of the widespread electrification of most of the developed or under development world, that started about one century ago.

The last decades, thousands of scientific publications surfaced, claiming diverging conclusions on the importance of the exposure of humans to these alternating electric and magnetic fields, either at higher or lower frequencies.

The debate especially on the interaction of Higher Voltage transmission lines at 50 or 60 Hz on humans is still open and various recommendations and subsequent corrections on the safety exposure levels have been issued from the International consulting authorities, such as the ICNIRP.

The above safety exposure levels consider only the thermal effects on the biological tissue, that is the temperature rise of the tissue due to the coupling with the alternating electric and magnetic fields.

The main scientific debate arises from the fact that many scientists claim also the existence of other effects, called biological ones, that may appear at exposure levels far below the recommended safe ones.

Several epidemiological studies have shown that there is a higher risk for specific diseases to appear to populations living closer to Higher Voltage, High Power transmission lines carrying alternating currents at 50 or 60 Hz, even at exposure levels far below the considered safe ones.

One weak point of the above studies is the practically impossible task to quantify this critical exposure level, both in amplitude and duration, since if any biological effect exists, this will appear after considerable time, probably months or years of exposure. During this period, the subjects living their everyday lifestyle, will be exposed to a multitude of different field amplitudes and for various durations, for which it is very difficult to evaluate their contribution to the claimed critical exposure level. Additionally, the immunity system of every individual reacts differently to repair any possible biological damage, which renders the evaluation of this critical exposure level even more difficult.

The scientific truth is that we do not know exactly how the alternating electric and magnetic fields interact with the living biological tissue, especially at the cellular level.

The latter, combined with the fact that humans have been exposed only for a very tiny fraction of their existence on the earth to such alternating electric and magnetic fields, has led many scientists and regulatory bodies to adopt the prudent avoidance attitude.

That is the less possible exposure, the better.

DISCLOSURE OF THE INVENTION

Technical Problem

In our everyday life activities, we are exposed to various alternating electric and magnetic fields in our home, work and commute environments, mainly but not exclusively, at the power distribution network frequencies of 50 or 60 Hz, depending on the specific spot on the globe.

The magnetic field components that we are exposed to, are usually very low for the typical home or working environment. An exception can be the commuting environment, especially with the rising use of electric transportation means, including electric cars. In this specific case, the alternating magnetic fields we are exposed to, can be of considerable amplitude and at higher frequencies, typically at the Kilohertz range or even higher. Usually, the duration of the exposure to these fields is relatively short for the everyday life of most subjects.

On the contrary, the electric field components in any electrified working, commuting, and living environment are more important than the magnetic ones. The main reason for this is because the magnetic field components are present only when loads are active at our vicinity. On the contrary, the electric field components are present continuously if electrified cables exist in the vicinity, independently from the current they carry. Therefore, the electric field components are present day and night, just on the condition that the environment is electrified, and the electrified cables not shielded, which is the rule all over the world.

Since we sit, move, stand and sleep within these environments, we are exposed to the electric field components of our electrified environment practically for the most part of our 24-hour living cycle.

While standing, we remain rarely still and therefore the components of the electric field generated by the electrified environment and coupled with our body change continuously, as also in the case that we walk in such an environment.

While sitting and sleeping, which is the majority state in our 24-hour living cycle, our body is coupled to all the electric field components generated mainly by the electric wires in our electrified environment, but also from various electric devices in the vicinity. The geometry of our body and its position in the space enclosed by the above sources, dictate the amplitude and phase of the components that are coupled with our body.

The coupling mechanism has been extensively studied and described by scientists who wanted to examine the interfering effects of such coupled fields to various biopotential measurements, such as the ECG (Electrocardiogram), as shown in the references [1] and [2].

Summarizing the literature, in the case of the electric coupling, as shown in FIG. 1, the human body 5 is considered to lie in between the two plates of a capacitor. The upper plate 1 of the capacitor is formed from the electrified wires 2 hidden in the ceiling and walls and therefore has the potential of the public power, namely 110 or 230V AC at most places of the globe, referenced to the ground. The lower plate 3 is formed from the floor and any conductive materials lying inside it, which are connected to the earth and/or the ground 4, directly or indirectly.

Even with one or more electrified conductors in the ceiling or walls, an equipotential three-dimensional surface is formed containing the conductors, since the corresponding wavelength of any electrical activity alternating at 50 or 60 Hz is much bigger than the typical conductor extension in a living or working environment, which represents the upper capacitor plate 1, shown as a plane surface for simplicity.

In the case of multiple electrified conductors and of multi-phase power systems (typical 3 phase systems), multiple equipotential three-dimensional surfaces exist, each with the corresponding power supply amplitude and phase. Each of these electrified equipotential surfaces is coupled with any conductive body and particularly with any human body in its vicinity, with its corresponding phase and amplitude.

The lower capacitor plate 3 is typically plane, following mainly the floor and is also considered equipotential for the same reason as above. However, for a complex working or commuting environment and in the general case, this ground or earth connected surface is also a three-dimensional one.

Since the human body 5 is conductive, its surface forms capacitive couplings, or capacitors, with each of the above equipotential surfaces. For simplicity, the conductive body or the human body is represented by the conductive cylinder 6.

In the simplest case, the conductive body and particularly the human body forms two capacitors C1 (7) and C2 (8) with its environment: C1 with the high voltage ceiling equipotential surface 1 and C2 with the floor equipotential surface 3, which is grounded. If both capacitors have the same value, then the body has a potential relative to the ground, equal to half the potential of the public power which electrifies the wires on the ceiling or walls. In general, the potential Vbody of the body depends on the ratio of the above two capacitors C1, C2 and is a fraction of the potential E and frequency f of the alternating power source 9.

Therefore, since in any electrified environment the conductive body and particularly the human body has a non-zero potential relative to the ground, it is continuously traversed by a current Ibody, also called displacement current. When a human sleep or sit, this current is practically constant. When a human stand or walk in such an environment, the amplitude and phase of the displacement current change continuously since the values of the above two capacitors C1, C2 also change.

Usually, the above current Ibody is very small and below the human perception threshold, for the typical electrified living environments. However, this is not always the case since it depends on both the amplitude and frequency of the source that the equipotential surfaces in the vicinity are connected to. Higher voltages or higher frequencies or both, may lead to important displacement currents flowing through the human body.

In the specific case that the human body is in conductive contact with the ground or earth, then its potential is much lower than the previous case of capacitive coupling with the earth, however, the displacement current Ibody becomes higher since the total impedance to the ground becomes smaller. This deliberate "grounding" of the human body is often used during ECG or other biopotential measurements, since it lowers the potential of the human body relative to the earth or ground and therefore minimizes the induced interference, although it maximises the displacement current through the body.

In the case of static electric fields, only transient displacement currents are developed inside any conductive or human body in its vicinity. These currents appear only when the amplitude of the electric field changes, or when the conductive or human body moves within the electric field. The coupling mechanism is the same as above and the amplitude of the displacement currents depend on the variation of the local amplitude of the field, the speed of motion of the body and the ratio of the capacitive couplings, as explained before.

Important static electric fields appear close to High Voltage DC power transmission lines, or to any working, living or commuting environment using high voltage dc power sources.

Magnetic coupling exists only when the electrified wires 21 conduct alternating current Iw, as shown in FIG. 2. The closed magnetic lines 23 that are formed around them, representing the generated magnetic field, if coupled with a conductive body and particularly with the human body 5, force the development of currents $I_E$ within the body, called eddy currents, which tend to compensate the field variations inside it, according to Faraday's law.

The developed currents inside the body depend mainly on the amplitude and frequency f of the field, usually 50 or 60 Hz at most parts of the globe. In a typical living environment, the expected magnetic fields are very low, since the usual currents are small. This may not be the case in a working environment or especially in a commuting environment, with the sharp increase of the electrical means of transportation, which involve important currents alternating at higher frequencies and therefore generating high amplitude, high frequency magnetic fields.

A new source of potential important exposure of humans to magnetic fields, is the increasing trend of wireless charging systems. Especially the in-house charging systems, active during many hours close to humans, are expected to couple magnetic fields of considerable amplitude at higher frequencies to humans standing or sleeping in their vicinity.

In the case of static magnetic fields, eddy currents are developed only when the conductive or human body moves within its field lines. The amplitude of the developed currents depends also on the magnetic permeability of the conductive body. In the case of the human body, which is paramagnetic, magnetic permeability is almost unity and therefore the developed eddy currents are small, except in the case of very high magnetic field amplitudes with important field gradients, which are not uncommon near high-end MRI scanners, or other devices using high static magnetic fields.

The scientific community has proposed solutions to avoid the important interference that also these coupled alternating magnetic fields may induce on the ECG or other recorded biological potentials.

It is important to note that in both cases, that is of the coupling of the electric field components and magnetic field components, the goal of the published techniques is to minimize the effects on the measured biopotentials, not to minimize the resulting displacement or eddy currents within the conductive or human body.

In the literature, the proposed solutions for the compensation of the effects of the coupled electric field components, apply a suitable potential on the human body, usually at the left leg, or literally connect the human body to the earth or ground through a resistor. The first technique changes suitably the potential of the body and the second minimizes the potential of the body relative to the ground or earth, just to minimize the interference produced by the coupled fields on the recorded biopotentials. In the first case, the displacement currents inside the body are also reduced, but in the second they become higher, as explained previously.

In the above case, the compensation potential or the ground potential is applied directly to the human body, using conductive electrodes like the ones used for recording the biopotentials, for the duration of the recording.

In the literature, the proposed solutions for the magnetic coupling do not include the human body, they just take care of the measuring cables, to avoid the induction of single mode potentials on the measuring devices. The typical solution is to minimize the distance between the measuring cables, so that the resulting loop has the minimum possible surface, which also minimizes the induced potential from coupled alternating magnetic fields and therefore also the resulting interference.

Since the coupling of magnetic fields with the human body itself does not produce interfering signals with the measured biopotentials, no care is taken, although the above magnetic fields induce eddy currents within the body.

Technical Solution

The scope of this invention is to provide contactless means for continuously eliminating the influence of the alternating coupled electric and magnetic fields to any conductive body and particularly to the human body, for the most part of the 24-hour life cycle.

To compensate the influence of the external alternating electric fields the invention utilises an intermediate conductive plate and active electronic circuits.

To compensate the external magnetic fields, the invention utilises peripheral coils and active electronic circuits.

Advantageous Effects

The invention eliminates the influence of the coupled electric fields to the human body in its range. It can be used continuously, covering practically most of the duration of the human 24-hour life cycle.

The invention eliminates the influence of the coupled magnetic fields to the human body in its range. It can be used continuously, covering practically most of the duration of the human 24-hour life cycle.

No contact is needed with the conductive or human bodies to operate.

The operation is automatic, seamless for the protected bodies and does not need any adjustment or calibration for its use.

BEST MODE FOR CARRYING OUT THE INVENTION

The invention utilizes two distinct compensation systems, one to compensate the electric field components and another to compensate the magnetic ones. The two compensation systems may have common or separated subsystems and may be independent or combined in the same apparatus. In the simplest embodiment shown here, the two compensation systems have common controller circuits, common power supplies and common voltage converters.

Figure 3:
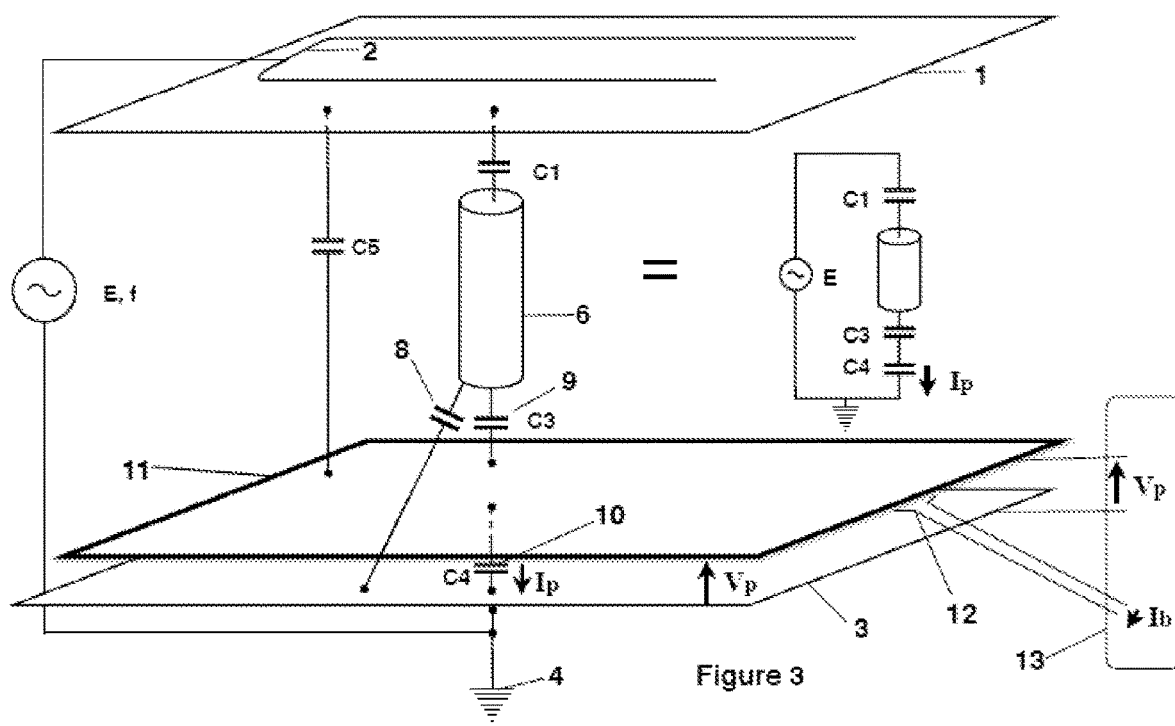
FIG. 3 describes the new coupling mechanism of the body with an electrified environment after the insertion of the intermediate plane, as well as the main connections to the compensation systems that minimize the electric and magnetic components coupled with the body.

The electric field components compensation system, as shown in FIG. 3, is constituted from the following two subsystems:

A conductive surface 11 placed between the body to protect 6 and the grounded plate 3, typically the floor. This surface is electrically isolated from both the body and ground.

A compensation system 13 including analog or digital or mixed components and subsystems and power sources, connected to the grounded plate 3 or ground 4 or earth and the above conductive surface.

The conductive surface 11 may have any convenient form or shape on the condition that it contains all or most of the possible projections of the bodies to protect to the earth or ground 4, typically the floor.

For simplicity, this conductive surface 11 is called from now on, intermediate plate.

For simplicity, the grounded plate, or earth, or the ground or if no ground or earth can be obviously defined near the bodies to protect, any main conductive neighbouring structure, from now is called ground 4.

The intermediate plate 11 must be isolated from the ground 4 and preferably also from the bodies 6 to protect.

The intermediate plate 11 may be constructed using any metal sheet, such as an aluminium foil or any other kind and should be isolated at its surfaces, as stated above.

Alternatively, any combination of interconnected conductive wires that may form an equipotential plane can be used as the intermediate plate.

Alternatively, any combination of interconnected conductive threads or strips or conductive liquid that extend to a surface hosting the bodies to protect can also be used as the intermediate plate.

Ideally, the intermediate plate should be a continuous conductive medium. However, for practical reasons "holes" are accepted, if the direct capacitive coupling 8 of the conductive body 6 to protect with the grounded plate 3 remains very small compared to the capacitive coupling 9 of the body 6 to the intermediate plate 11. This allows an infinite number of combinations of the above conductive wires or strips or plates or conductive liquid to form the intermediate plate.

A preferred embodiment of the conductive equipotential surface in the case of bodies lying on a bed, is a mattress or a sheet or any other bed cover including interconnected conductive threads or wires or strips, or conductive liquid. Similarly, any metallic springs or spring system supporting the mattress can be used as the intermediate plate, on the condition that they are electrically interconnected and isolated from the ground and the bodies.

A preferred embodiment of the intermediate plate in a working or living environment is any form of carpet or floor containing interconnected conductive threads or wires or strips or plates or conductive liquid, as explained above. For optimum protection, it must contain most or all possible projections of the bodies to protect to the ground. All conductive parts of the intermediate plate must be isolated from the ground.

A preferred embodiment of the intermediate plate in the case of a commuting environment could also be in the form of a carpet or in case that this is difficult to implement, in the form of a seat cover or support or intermediate seat, or any other suitable form on which the body sits or stands, containing interconnected conductive threads or wires or strips or plates or conductive liquid as explained above. All conductive parts of the intermediate plate must be isolated from the bodies and the vehicle ground, typically from its chassis or main conductive frame, or the electric equipment ground.

A preferred embodiment in the case of a very intense or high alternating frequency electric field environment could also be an intermediate plate in the form of open clothes, covering from a convenient distance part or most of the body to protect, containing interconnected conductive threads or wires or strips or plates or conductive liquid as explained above, all isolated from the body and the ground and allowing the body to move freely. In case that all the parts of the body are covered, then the above surface is not any more an intermediate plate, but rather a Faraday cage and therefore it must be connected directly to the ground to be effective, as is already known from the literature. However, within a Faraday case the movement of the body is highly restricted.

Generally, in most of the typical living working and commuting environments, a rigid or flexible quasi-plane shape of the intermediate plate, manufactured as explained above, protects efficiently the bodies contained within its limits. To accommodate for less usual living, working or commuting environments, the intermediate plate may have any shape to include the bodies to protect. As an example, it could have side extensions if the bodies need to be near grounded or earthed side structures. The general rule is to avoid most of the possible secondary direct capacitive couplings 8 of the body to the ground and replace them by capacitive couplings 9 to the intermediate plate.

Figure 1:
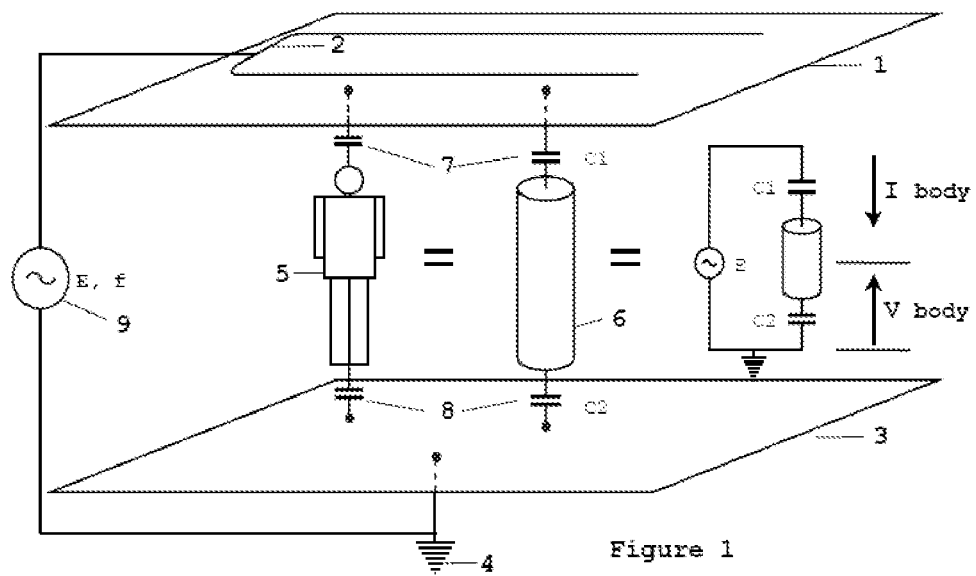
FIG. 1 describes the capacitive coupling mechanism of the body with an electrified environment.
Figure 2:
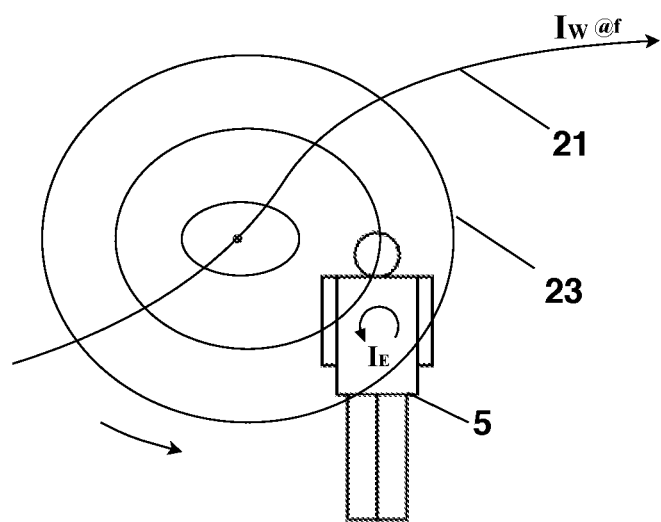
FIG. 2 describes the magnetic coupling mechanism of the body with an electrified, current carrying environment.

The role of the proposed intermediate plate 11 is to substitute the ground, or floor capacitor plate 3 in the coupling model of the body in an electrified environment, as described in detail above and shown in FIG. 1. Therefore, in the new equivalent electrical environment as shown in FIG. 3, after the insertion of the intermediate plate 11, the capacitive coupling C1 of the body to the high potential plate 1 remains practically the same as before, but the capacitive coupling with the ground is substituted by the capacitive coupling C3 of the body 6 to the inserted intermediate plate 11.

The intermediate plate 11 has also a capacitive coupling C4 with the ground plate 3. Therefore, the equivalent electrical circuit that models now the electrified environment containing conductive bodies and particularly human bodies, is represented by three capacitive couplings. One from the body (or bodies) 6 to the high potential surfaces 1, noted as C1, which remain practically the same as before inserting the intermediate plate. One from the body (or bodies) 6 to the intermediate plate 11, noted as C3, and a third one between the intermediate plate 11 and the grounded plate 3, or the chassis in the case of a vehicle, or the most important conductive mass of a structure, in case the above cannot be defined precisely, noted as C4. For completeness of the equivalent circuit, capacitor C5 between the high potential plate 1 and the intermediate plate 11 is also shown, which however does not affect the body current and is therefore neglected.

The main role of the body current compensation system is to measure the potential Vp of the intermediate plate, and/or the current Ip flowing from the intermediate plate to the ground and actively minimize them to practically zero amplitude value. From simple circuit theory, when this current Ip is zero, also the displacement currents through the other two series capacitive couplings C1 and C3 are zero. Therefore, also any conductive bodies and particularly any human bodies that are protected by the present invention will experience practically zero currents through them, if they sleep, stay, or move within the limits of the intermediate plate.

The magnetic field components compensation system, as shown in FIG. 3, is constituted from the following two subsystems:

A plane coil system 12, positioned at the periphery of the intermediate plate 11. To fully compensate any possible coupled magnetic fields in the space to protect, an orthogonal three-coil measuring, and compensation system should be implemented. However, for simplicity, for easiness of movement and mainly to cover the most important field components especially while sleeping, a coil system 12 at the periphery of the intermediate plate is preferred.

A compensation system 13 including analog or digital or mixed components and subsystems and power sources, connected to the coil system 12.

Figure 4:
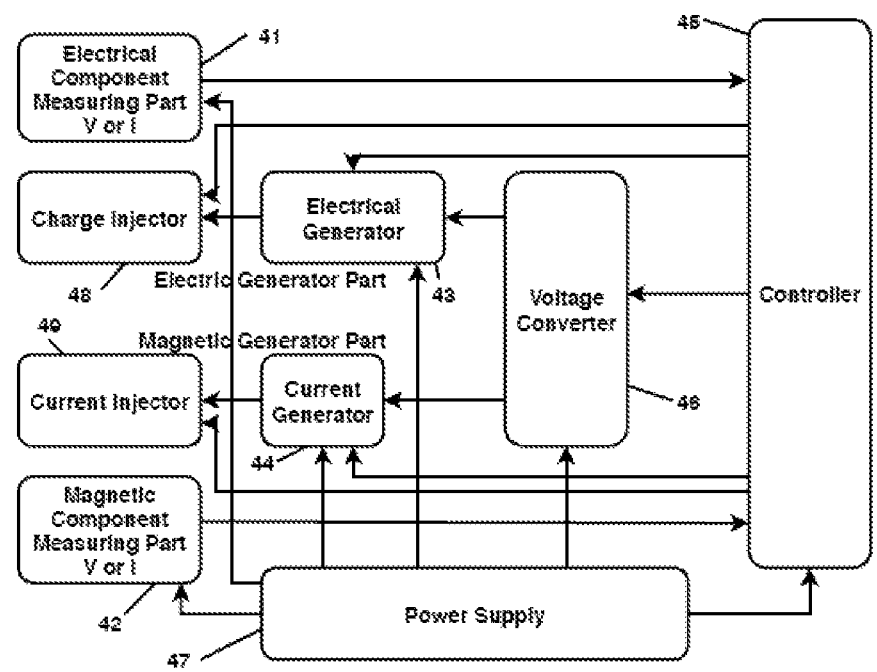
FIG. 4 describes the functional parts of the compensation systems of the invention.

The body current compensation system 13 contains typically but not restricted to, the following parts, as shown in FIG. 4. The electric component measuring part 41, which measures the potential and the current of the intermediate plate to the ground, as explained above. The magnetic component measuring part 42, which measures the magnetic flux that any external alternating magnetic field couples to the intermediate plate. The electrical generator part 43, that produces a suitable waveform in phase and amplitude to apply on the intermediate plate, to actively compensate its potential. The magnetic generator part 44, that produces a suitable current to actively compensate the coupled magnetic components. The control part 45, that measures, controls, adjusts, analyses, communicates with the user or any other systems in any convenient way and performs all necessary tasks for the evaluation of the couplings and the efficient minimization of the displacement currents and the induced magnetic fields. The voltage converter part 46, that provides the necessary voltage and current levels to feed the generators. The power supply 47 and the energy source, that feed all the above subsystems.

The electric component measuring part 41 measures the potential across a high value resistor connected from the intermediate plate to the ground. It may also contain a sensitive current measuring system of the current flowing the above resistor as a main or complementary means of the active current minimization control system. Alternatively, it may contain a very high input impedance amplifier instead of the above high value resistor, to measure the potential and/or the current flowing directly from the intermediate plate to the ground.

The magnetic component measuring part 42 uses a coil of one or more flexible or rigid isolated turns, preferably at the periphery of the intermediate plane, terminated to a resistor. It may contain an amplifier to amplify the potential developed across the resistor which corresponds to the coupled magnetic flux within the measuring loop. It may also contain a sensitive current measuring system to measure the current of the loop, which will be actively minimized by the proposed control system.

In the case of commuting or working environments where important magnetic fields are present, an orthogonal three-coil system, or smaller local coils are necessary to fully compensate the induced magnetic fields. Therefore, multiple similar independent magnetic components measuring systems are necessary, as well as multiple magnetic generators.

The electrical generator part 43 produces the suitable waveform which will be applied to the intermediate plate through the charge injector 48 to actively minimize its potential to the ground and therefore also its current to the ground. The generator provides charges to the intermediate plate with the needed rate and sign to effectively fulfil the above goal. In a simplified way, the generator provides an out of phase current to the intermediate plate with the same amplitude, to the one developed from the capacitive coupling of the intermediate plate with the conductive bodies and the possible various electrified equipotential surfaces within its limits. This results in an active minimization of the potential of the intermediate plate to the ground.

The simplest means of injecting the above charges is through a series resistor from the generator 43 to the intermediate plate. Another more efficient way to materialize the charge injector 48, is using a higher frequency switching circuit, in half or full bridge topology, coupled through a low pass filter to the intermediate plate, functioning in current mode.

Since the potential of the electric coupling alternates at the frequency of the local sources, also negative potential values corresponding to the ground are necessary for the efficient compensation of the displacement currents. Typically, but not restricted to, the generator 43 is a dc-dc converter, able to provide the necessary positive or negative currents or charges. The operating bandwidth of the generator depends mainly on the rate of change of the power sources that electrify the environment. Typically, for a living environment a bandwidth of a few KHz is enough. However, mainly but not restricted to, in a commuting or industrial working environment the bandwidth should be extended to cover sufficiently the higher expected spectral components of any possible power sources in the vicinity.

Each magnetic generator part 44 feeds through the current injector 49 the magnetic measuring coil, or a second separate but similar compensation coil, with a current of the suitable phase and amplitude to minimize the total magnetic flux through the measuring loop. By minimizing the flux crossing the intermediate plate, this also minimizes the corresponding flux component through any conductive body or bodies within its perimeter. The generated currents must be bipolar to compensate efficiently the alternating magnetic fields.

Typically, but not restricted to, each magnetic generator 44 is a dc-dc converter able to provide bipolar potentials. The operating bandwidth of the generator depends mainly on the rate of change of the power sources that electrify the environment. Typically, for a living environment a bandwidth of a few KHz is enough. However, mainly but not restricted to, in a commuting or industrial working environment the bandwidth should be extended to cover sufficiently the higher expected spectral components of any possible power sources in the vicinity.

In its the simplest embodiment, each current injector 49 contains only a series resistor connecting the current generator to the to the coil. A more efficient way is using a higher frequency switching circuit, in half or full bridge topology, coupled with a low pass circuit to the coil or coils, functioning in current mode.

The control part 45 may be realized with either analog or digital or mixed components and subsystems. The main role of the control part is to measure the above electric and magnetic potentials developed by the corresponding couplings on the intermediate plate and coils and then to apply the correct commands and/or waveforms to the electric and magnetic generators, to minimize the displacement currents and the induced magnetic fields. The applied waveforms are part of a control loop reading continuously the corrected electric and magnetic potentials and/or the current components developed on/through the terminating resistors, of the corresponding measuring parts. The control loop has as target to minimize the corresponding potentials and/or the currents on the sensing resistors or other suitable terminating or measuring devices of the measuring parts. Additionally, the control part 45 communicates with the user or any other systems in any convenient way and performs any other necessary tasks for the efficient minimization of the displacement currents and the induced magnetic fields.

The voltage converter part 46 provides the necessary voltage levels to the electric generator 43 and the magnetic generator 44, converting the potential of the available power source to a suitable potential allowing the compensation of the electric and magnetic components, as described above.

In a typical sleeping environment, the potential of the human body lying on a bed can be as high one third of the potential of the low voltage public distribution system, that is around 35 or 75V AC RMS, in most parts of the globe. In the simplest form of embodiment of the present invention, the electrical generator should be fed with a typical peak potential of at least 50 or 106V, with both negative and positive signs, to actively compensate through a resistor the potential of the intermediate plate and therefore minimize the total current, in this typical scenario. The role of the voltage converter 46 is to provide this potential to the electric generator 43. For different electrified environments, or bodies or couplings, this potential varies, therefore the converter should be able to adapt to any new environment, preferably automatically. The corresponding current is typically very low, in the order of micro to milli A and therefore the power drown from the voltage converter 46 is also very small. In the preferred embodiment, the voltage converter 46 adapts automatically the delivered potential to any new electrified environment, as necessary for the system to compensate continuously the displacement currents, as explained above.

The power needed from the current generator(s) 44 is typically very small, since the compensation currents fed to the loop are also very small in a typical living and working environment. This is not the case for the commuting environment, where higher currents, usually alternating at higher frequencies, could be needed for effective magnetic field compensation. In the simplest invention embodiment, the current generator(s) 44 could be fed directly from the potential of the power supply. Alternatively, especially for higher energy efficiency of the system, the voltage converter part 46 could provide the current generator 44 with lower potential than the one offered from the power supply 47.

The power supply part 47 provides all the necessary energy for the function of all the above subsystems and parts. The energy source may be any available source, that is an isolated low voltage power supply from the public power, a battery, or any other galvanically isolated convenient source.

As explained above, the typical living and working environments have mostly coupled electric components and negligible magnetic ones. On the contrary, in commuting or industrial environments, coupled magnetic components could be of much higher importance than the electric ones. Therefore, for simplicity and lower cost, in the case of need of higher magnetic field component compensation, with minimal need for electric field component compensation, or inversely, the described invention can include only the magnetic or only the electric field compensation system, as described above.

REFERENCES

[1] J. C. Huhta and J. G. Webster, "60-Hz Interference in electrocardiography,"

IEEE Trans. Biomed. Eng., vol. BME-20, pp. 91-101, 1973.
[2] N. V. Thakor and J. G. Webster, "Ground-free ECG recording with two electrodes,"
IEEE Trans. Biomed. Eng., vol. BME-27, pp. 699-704, 1980.

The invention claimed is:

1. A body current compensation system for electrically induced currents, comprising:
   an intermediate conductive plane between a conductive body or bodies to protect a ground;
   a sensor to sense the electrically induced currents from, or a potential of the intermediate conductive plane relative to the ground;
   electronic circuits to measure the electrically induced currents or the potential of the intermediate conductive plane relative to the ground;
   electronic circuits to generate electric charges of positive or negative sign;
   electronic circuits to inject the electric charges to the intermediate conductive plane;
   electronic circuits to minimize continuously the electrically induced currents or the potential of the intermediate conductive plane, relative to the ground;
   a controller to communicate with the user or other control systems directly or via a cloud; and
   an isolated power supply to feed all the electronic circuits and the sensor.

2. The body current compensation system for the electrically induced currents as of claim 1, wherein the intermediate conductive plane is made of a continuous conductive plate, or electrically connected separate conductive elements, wherein the electrically connected separate conductive elements comprise woven conductive wires, conductive stripes, conductive plates, conductive threads, or a conductive liquid.

3. The body current compensation system for the electrically induced currents as of claim 1, wherein the intermediate conductive plane is isolated from the body or bodies to protect and the ground.

4. The body current compensation system for the electrically induced currents as of claim 1, wherein the intermediate conductive plane has a surface and shape adequate to include all or most projections of the body or bodies to protect to the ground.

5. The body current compensation system for the electrically induced currents as of claim 1, wherein the sensor is a resistor between the intermediate conductive plane and the ground.

6. The body current compensation system for the electrically induced currents as of claim 1, wherein the electronic circuits to measure the electrically induced currents or the potential of the intermediate conductive plane to the ground is an input impedance operational or differential or instrumentation amplifier.

7. The body current compensation system for the electrically induced currents as of claim 1, wherein the electronic circuits to generate electric charges of positive or negative sign is a dc-dc converter.

8. The body current compensation system for the electrically induced currents as of claim 1, wherein the electronic circuits to inject the charges to the intermediate conductive plane is a resistor.

9. The body current compensation system for the electrically induced currents as of claim 1, wherein the electronic circuits to inject the charges to the intermediate conductive plane has a half or full bridge topology.

10. The body current compensation system for the electrically induced currents as of claim 1, wherein the electronic circuits to minimize continuously the electrically induced currents or the potential of the intermediate conductive plane, relative to the ground is an analog error amplifier or a digital controller with analog to digital inputs and digital to analog outputs.

11. The body current compensation system for the electrically induced currents as of claim 1, wherein the controller to communicate with the user or other control systems directly or via a cloud is a bidirectional wireless communication system.

12. The body current compensation system for the electrically induced currents as of claim 1, wherein the controller to communicate with the user is a display with virtual or physical selection buttons.

13. The body current compensation system for the electrically induced currents as of claim 1, wherein the isolated power supply to feed all the electronic circuits and the sensor is a battery stack with rechargeable or non-rechargeable elements.

14. The body current compensation system for the electrically induced currents as of claim 1, wherein the isolated power supply to feed all the electronic circuits and the sensor is a galvanically isolated power supply connected to a grid power.

15. A body current compensation system for magnetically induced currents comprising:
    a coil at a periphery of an intermediate conductive plane;
    a sensor to sense the magnetically induced currents or a potential induced to the coil;
    electronic circuits to measure the magnetically induced currents or the potential induced to the coil;
    electronic circuits to generate electric currents of positive or negative sign;
    electronic circuits to inject the electric currents to the coil;
    electronic circuits to minimize the magnetically induced currents or the potential induced to the coil;
    a controller to communicate with the user or other control systems directly or via a cloud; and
    a galvanically isolated power supply to feed all the electronic circuits and the sensor.

16. The body current compensation system for the magnetically induced currents as of claim 15, wherein the coil at the periphery of the intermediate conductive plane serves both for detecting and compensating the magnetically induced currents.

17. The body current compensation system for the magnetically induced currents as of claim 15, wherein two independent coils at the periphery of the intermediate conductive plane exist, one for detecting and the other for compensating the magnetically induced currents.

18. The body current compensation system for the magnetically induced currents as of claim 15, wherein the sensor to sense the magnetically induced currents or the potential induced to the coil is a resistor connected to a terminal of the coil.

19. The body current compensation system for the magnetically induced currents as of claim 15, wherein the electronic circuits to measure the magnetically induced currents or potential induced to the coil are operational or differential or instrumentation amplifiers.

20. The body current compensation system for the magnetically induced currents as of claim 15, wherein the electronic circuits to generate electric currents of positive or negative sign are dc-dc converters.

21. The body current compensation system for the magnetically induced currents as of claim 15, wherein the electronic circuits to inject the electric currents to the coil are resistors.

22. The body current compensation system for the magnetically induced currents as of claim 15, wherein the electronic circuits to inject the electric currents to the coil are a half or full bridge topology.

23. The body current compensation system for the magnetically induced currents as of claim 15, wherein the electronic circuits to minimize the magnetically induced currents or the potential induced to the coils are analog error amplifiers or digital controllers with analog to digital inputs and digital to analog outputs.

24. The body current compensation system for the magnetically induced currents as of claim 15, wherein the controller to communicate with the user or other control systems directly or via the cloud is a bidirectional wireless communication system.

25. The body current compensation system for the electrically induced currents as of claim 15, wherein the controller to communicate with the user is a display with virtual or physical selection buttons.

26. The body current compensation system for the magnetically induced currents as of claim 15, wherein the isolated power supply to feed all the electronic circuits and the sensor is a battery stack with rechargeable or non-rechargeable elements.

27. The body current compensation system for the magnetically induced currents as of claim 15, wherein the isolated power supply to feed all the electronic circuits and the sensor is a galvanically isolated power supply connected to the grid power.

* * * * *